(12) United States Patent
Martin

(10) Patent No.: US 7,564,558 B2
(45) Date of Patent: Jul. 21, 2009

(54) GAS CELL

(75) Inventor: Hahs Evald Goran Martin, Delsbo (SE)

(73) Assignee: Senseair AB, Delsbo (SE)

( * ) Notice: Subject to any disclaimer, the term of this patent is extended or adjusted under 35 U.S.C. 154(b) by 391 days.

(21) Appl. No.: 11/192,465

(22) Filed: Jul. 18, 2005

(65) Prior Publication Data
US 2005/0287041 A1    Dec. 29, 2005

(30) Foreign Application Priority Data
Jan. 15, 2003    (WO) ................ PCT/SE2004/000038

(51) Int. Cl.
  *G01N 21/00*    (2006.01)
  *G01N 33/00*    (2006.01)
(52) U.S. Cl. ................ 356/437; 356/432; 356/246; 422/83
(58) Field of Classification Search ......... 356/432–444, 356/301, 246; 250/222.2, 343, 437, 573; 422/54, 67, 82.05
See application file for complete search history.

(56) References Cited

U.S. PATENT DOCUMENTS

| | | | | |
|---|---|---|---|---|
| 4,784,486 A | * | 11/1988 | Van Wagenen et al. | 356/301 |
| 5,450,193 A | * | 9/1995 | Carlsen et al. | 356/301 |
| 5,461,477 A | * | 10/1995 | Marinelli et al. | 356/454 |
| 5,550,375 A | * | 8/1996 | Peters et al. | 250/343 |
| 5,807,750 A | * | 9/1998 | Baum et al. | 436/164 |
| 6,016,203 A | * | 1/2000 | Martin | 356/432 |
| 6,194,735 B1 | * | 2/2001 | Martin | 250/573 |
| 6,943,885 B2 | * | 9/2005 | Martin | 356/437 |

* cited by examiner

*Primary Examiner*—Sang Nguyen
(74) *Attorney, Agent, or Firm*—John Lezdey

(57) ABSTRACT

The present invention relates to a gas cell which is included in a gas sensor and adapted to establish the presence of a gas and/or for determining the concentration of one such gas (G), comprising a cavity (2') which is delimited by wall portions that have light reflecting properties and which is intended to enclose a volume ((G)) of said gas, and further comprising a light source (3) which is adapted to emit a light bundle (3a') directed for reflection between cavity-associated and opposing wall portions, wherein a light bundle (3a") is comprised of light rays which are reflected in a concave wall mirror surface (2b') and adapted to be directed onto one or more light receivers (4, 5) which function to detect an absorption wavelength corresponding to the gas sample ((G)). The concave curved wall mirror surface (2b') is adapted to reflect an obliquely received divergent light bundle (3a') from the light source (3) onto a flat grating-allocated cavity-associated wall surface (2g') whose reflecting surface includes or is structured as a Littrow arrangement (2g"). The light bundle (3a") is adapted to fall onto the flat wall surface (2g') at an angle which lies close to the Blaze angle of the grating wherewith, inter alia, an absorption wavelength corresponding to the chosen gas sample ((G)) and present in the light bundle (3a") is caused to be reflected and diffracted ((3a")) by said flat wall surface (2g") in a straight opposite direction so as to be reflected again in said curved mirror surface (2b') and directed diffracted towards each of said light receivers (4, 5).

27 Claims, 3 Drawing Sheets

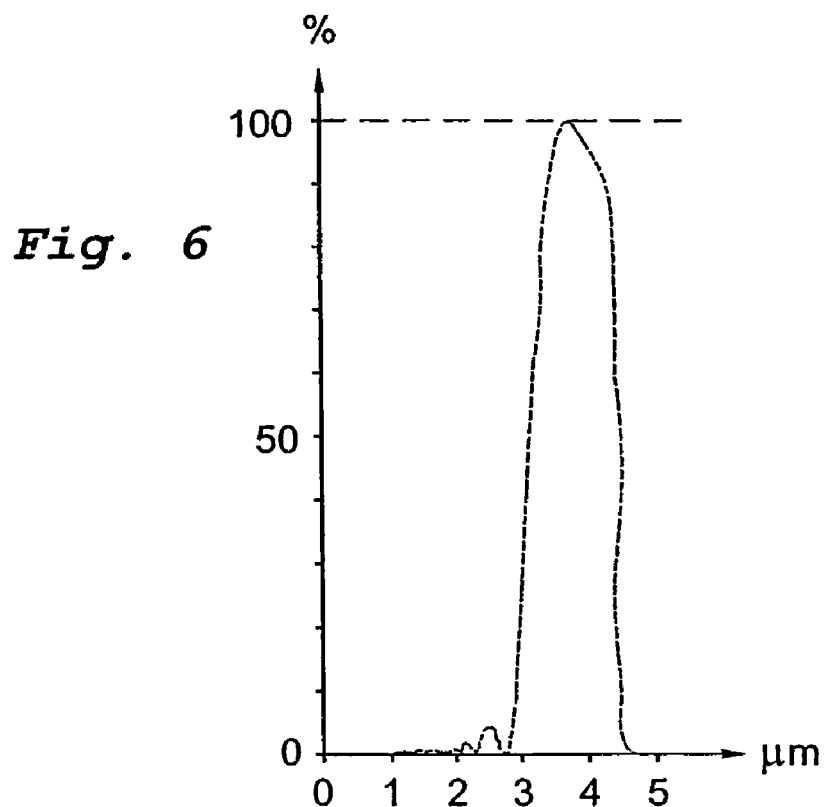
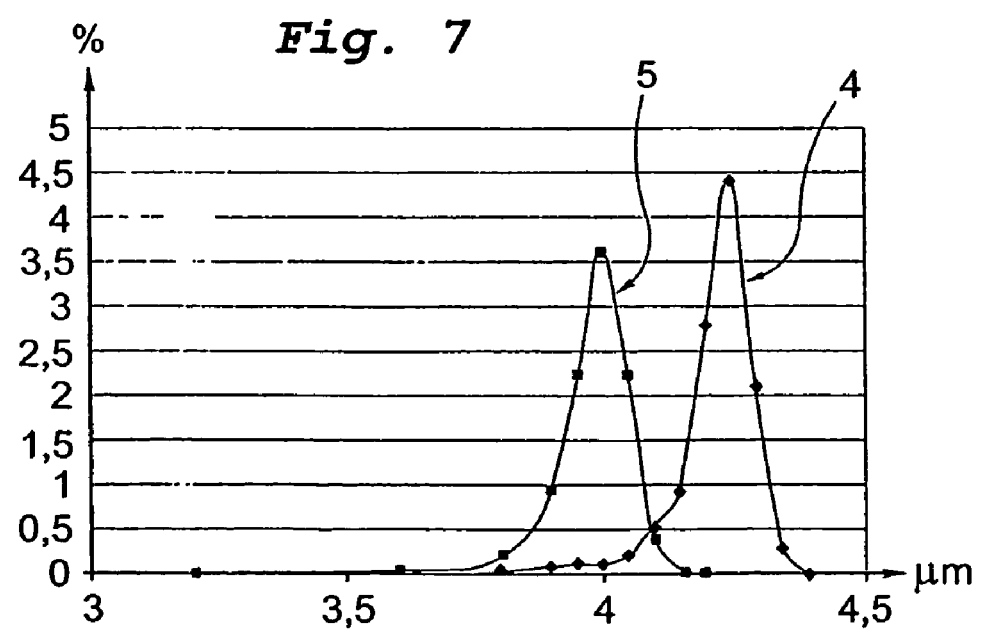

GAS CELL

TECHNICAL FIELD

The present invention relates generally to a gas cell and more particularly to a gas cell that is included in a gas sensor and adapted to determine the presence of a gas and/or a gas mixture and/or the concentration of such a gas and/or gas mixture, with the aid of spectral analysis of light waves that have one or more different absorption frequencies.

It also lies within the scope of the invention to determine the presence of a plurality of gases in a gas mixture, each of which gases may be related to one or more absorption frequencies.

The inventive gas cell is adapted to co-act with electronic circuits as a unit, said circuits enabling a gas cell light source to be driven and signals occurring on one or more light receivers to be sensed.

Each of the light receivers is adapted for evaluation of the instant light intensity occurring in respect of one or more chosen wavelengths and to evaluate the presence of one or more chosen gases and/or the concentration of said gas or gases, on the basis thereof.

One or more of these light receivers may conveniently be used as a reference signal.

A display unit is connected to the electronic circuits, for indicating visually the presence of a gas and/or its concentration.

Gas cells of this kind include a light reflecting facility, which includes a cavity defined by wall portions and intended to enclose a volume of said gas or gas mixture for assaying or measuring purposes.

Gas cells of this kind also include or co-act with a light source, preferably one which generates and emits light within the visible frequency range or, in the case of certain applications, light in the IR range, and which is adapted to emit a light bundle which is directed so as to be reflected between mutually opposite wall portions of said cavity.

With the aid of requisite reflective elements, the light bundle shall be comprised of diverging light beams or light rays which are directed onto and reflected by a concave-curved wall portion so as to be able to converge onto one or more light receivers with the aid of said wall portion.

Such a light receiver is adapted through the medium of electronic circuits to sense the light intensity in respect of its chosen light-absorbing wavelength or wavelengths within a light spectrum corresponding to said gas, by utilising a reduction of a given gas-significant wavelengths, said reduction being significant in respect of spectral analysis.

Light receivers of this kind are connected to electronic circuits to enable the intensity of the wavelengths of the light spectrum to be evaluated and also to sense the intensity of a reference wavelength related to the light intensity concerned in relation to the light source.

BACKGROUND OF THE INVENTION

Several different types of methods and arrangements of the aforesaid nature are known to the art.

A gas sensor that utilises an infrared (IR) spectrometer technique in accordance with U.S. Patent Publication U.S. Pat. No. 5,550,375 can be mentioned as a first example of the technical background of the invention and the technical field to which the invention belongs.

This prior publication illustrates and describes an arrangement which, in principle, utilises the possibility of detecting a gas and/or the concentration of the gas selectively with the aid of an IR spectrometer, by establishing the specific absorption wavelengths of the gas and evaluating the intensity of the gas in its gas-significant wavelengths within the infrared spectral region.

The gas sensor illustrated in said prior publication is particularly adapted for the continuous control of a gas flow or a gas-filled cavity, where the sensor or cell body is comprised of one single part and is produced as a body of microstructure.

The cavity in the gas cell includes a wall-related mirror grating placed between the input and output openings for beams of infrared light.

According to the embodiment, illustrated in FIG. 1B, a light bundle having divergent light rays is emitted from the light source (7) through a gap or opening (3) onto a first concave mirror surface (5) from which it is reflected obliquely onto a planar grid or grating surface (2) and there reflected or diffracted obliquely as a light wave onto an adjacent concave second mirror surface (8) so as to be able to pass through the output opening (4) as a convergent light bundle.

It is shown that the body or a gas-cell base plate (1) can be produced via X-ray, lithographic etching, electroplating and moulding processes, via the LIGA process.

The gas sensor shown and described in the International Patent Publication WO-A1-98/09152 is another example of the technical background and the technical field applicable to the present invention.

This latter prior publication illustrates a gas sensor (A) adapted for evaluating the composition of a gas sample enclosed in a cavity (2) or in a gas cell.

The gas cell has been shown in the form of a block, where cavity walls and cavity wall sections are said to have a very high light reflecting ability and are designated mirror surfaces (11A, 12A).

The cavity (2) includes an opening (2a) for incoming light rays which shall be reflected within the cavity a predetermined number of times such as to define a requisite measuring path or extremity before exiting through an output opening (6).

More particularly, the prior publication teaches the use of three mutually opposite and concave light-reflecting wall portions (11, 12, 13) in the gas cell.

A first wall portion (11) has the form of a semi-ellipse or ellipsoid.

A second (12) and a third (13) of said wall portions have a similar form, conforming to a part of a semi-ellipse or ellipsoid.

SUMMARY OF THE PRESENT INVENTION

Technical Problems

When taking into consideration the technical deliberations that a person skilled in this particular art must make in order to provide a solution to one or more technical problems that he/she encounters, it will be seen that it is necessary initially to realise the measures and/or the sequence of measures that must be undertaken to this end, and also to realise which means is/are required to solve one or more of said problems. On this basis, it will be evident that the technical problems listed below are highly relevant to the development of the present invention.

When considering the present state of the art, as described above, it will be seen that a technical problem resides in the ability to realise the significance of and the advantages associated with creating a gas cell for inclusion in or connection to a gas sensor that can include the requirements given in the introduction and that may be given a very compact form while, nevertheless, providing a sufficiently long optical measuring path or extremity within the cavity of the gas cell so as to enable an accurate spectral analysis to be carried out with the aid of one or more relevant absorption wavelengths in respect of a given gas or certain selected gases with the aid of electronic circuits.

It will also be seen that a technical problem resides in creating with simple measures and simple means conditions that will enable one or more gases and/or one or more gas concentrations to be evaluated as desired, with a high degree of resolution and a high degree of efficiency.

It will also be seen that a technical problem resides in the measures required to significantly increase the length of the measuring distance or path, and to use primarily a reflector construction for the light source used to this end.

An additional technical problem resides in the ability of realising the significance of and the advantages afforded by using primarily an optical measuring path, occurring within the gas-sample cavity, by which light is reflected and diffracted, and secondly utilise a further optical measurement path, occurring in said reflector construction.

There then resides the technical problem of being able to realise the significance of and the advantages afforded by creating a gas cell of such geometrical shape and including a gas-sample and light-reflecting cavity that will enable one or more light receivers to be placed, although side-related in front of an omniradiating light source, or side-related slightly in front of, on one side of, or slightly behind a reflected fictive or virtual light source.

A technical problem also resides in the ability to realise the significance of and the advantages afforded by placing a selected number of, such as at least two, light receivers adjacent to and externally of a reflector construction and adjacent to and externally of a converging and/or diverging light bundle, sent via the light source reflector.

A technical problem also resides in the ability to realise the significance of and the advantages afforded by adapting a cavity-forming concave wall portion to reflect an oblique and slightly incident divergent light bundle received from the light source onto a planar grating-allocated cavity wall portion.

A further technical problem resides in the ability to realise the significance of and the advantages afforded by allowing a planar wall portion and its reflecting and diffracting surface to include or be structured as a known "Littrow" arrangement.

Another technical problem resides in the ability to realise the significance of and the advantages afforded by giving the curved light-reflecting surface a shape which conforms to the shape and curvature of a section of a parabolic line and therewith realise that the planar light-reflecting and grating-allocated wall portion shall define an angle which creates conditions to allow a diffracted wave front to be reflected.

Still a further technical problem resides in the ability to realise the significance of and the advantages afforded by creating in said cavity conditions such that the light bundle or the wave front is caused to fall onto said planar wall portion at a chosen angle, namely an angle that lies close to a "Blaze" angle assigned to the grating.

A technical problem also resides in the ability to realise the significance of and the advantages afforded by causing one or more wavelengths present in the light bundle and corresponding to the chosen gas or gases to be reflected and deflected by said planar wall portion in a "straight" opposite direction so that the light will again be reflected as a diffracted wave front in said curved surface and therewith allowed to reflect a chosen wavelength or chosen wavelengths in a direction towards said light source, although slightly to one side thereof.

A technical problem also resides in the ability to realise the significance of and the advantages afforded by allowing said curved wall portion to conform to a part of the curved shape formed by a parabolic line or a parabolic arc.

In this regard, a technical problem is believed to reside in the ability to realise the significance of and the advantages afforded by allowing said part of the curved shape to lie close to the vertex of a parabolic line and also close to the focusing point of said line.

A technical problem also resides in the ability to realise the significance of and the advantages afforded by delimiting said part of said curved shape by a point or a section orientated at right angles to the axis of a parabolic line and through an axis-related focal point.

A technical problem also resides in the ability to realise the significance of and the advantages afforded by allowing the image of a physical light source to be placed virtually or to appear in or adjacent to a focus or focal point of a parabolic shape via a reflector construction.

It will also be seen that a technical problem resides in the ability to realise the significance of and the advantages associated by allowing the curved wall portion of said cavity to have the form of that part of a parabolic arc that is orientated solely on one side of the axis of a parabolic shape.

It will also be seen that a technical problem is one of realising the significance of and the advantages afforded by allowing the planar grating-allocated wall portion of the cavity to include a grating structure having a Blaze angle for providing reflection and diffraction in an essentially straight opposite direction.

A technical problem also resides in the ability to realise the significance of and the advantages afforded by adapting the grating structure and other measures to provide solely a diffraction grating of a first order.

Still another technical problem resides in the ability to realise the significance of and the advantages afforded by choosing a Blaze angle of between 50 and 60°.

It will also be seen that a technical problem resides in the ability to realise the significance of and the advantages afforded by placing one or more light receivers adapted for diffracted wavelengths to be placed close to the physical light source and/or close to the virtual light source, with their receiving lobes directed towards associated surface sections within the parabolically curved surface.

Another technical problem resides in the ability to realise the significance of and the advantages afforded by creating conditions, which allow a plurality of light receivers to be placed adjacent a focus or a focal point for said parabolic shape.

Another technical problem resides in the ability to realise the significance of and the advantages afforded by forming said cavity from two polymer-based replicas that have been treated to give chosen wall portions light-reflecting properties.

A technical problem also resides in the ability to realise the significance of and the advantages afforded by allowing the light source used to consist of an incoherent light source, for generating a wavelength spectrum within the IR range.

Yet another technical problem resides in the ability to realise the significance of and the advantages afforded by allowing a physical light source or a virtual light source to be placed in or adjacent to a focus or a focal point associated with the parabolically curved concave surface.

A technical problem also resides in the ability to realise the significance of and the advantages afforded by placing one or more light receivers in the close proximity of a focal point allocated to the parabolically curved concave surface or in said focal point.

A technical problem also resides in the ability to realise the significance of and the advantages afforded by placing a physical light source in one focus or focal point of an ellipsoidal shape and by placing an optical filter, adapted to the detector system, in or close to a virtual light source appearing in a second focus or in a second focal point.

A technical problem also resides in the ability to realise the significance of and the advantages afforded by adapting the optical filter to permit the passage of light-related wavelengths within a free spectral region applicable to the detector system.

Yet another technical problem resides in the ability to realise the significance of and the advantages afforded by adapting said optical filter to filter out or to block wavelengths that are shorter than those wavelengths that are co-ordinated within the free spectral region applicable to the chosen detector system.

Solution

The present invention takes as its starting point the aforementioned known technique in which a gas sensor is designed to determine the presence of one or more gases and/or is designed to determine the concentration of said gases.

The gas sensor requires the use of a gas cell that includes a cavity, which is defined by wall portions that have light reflecting properties and which is intended to enclose a first volume of said gas to be measured, and that also includes a light source which is adapted to emit a light bundle directed for reflection between opposite wall portions of said cavity, where said light bundle is formed, inter alia, by divergent light rays that are reflected in a concave wall portion and directed towards one or more light receivers, and which sense the occurring light intensity of one or more significant absorption wavelengths corresponding to said gas, through the medium of electronic circuits.

With the intention of solving one or more of the aforesaid technical problems, it is proposed, in accordance with the invention, that the known technique is modified by adapting said concave curved wall portion to reflect an oblique light bundle received from the light source onto a planar grating-allocated wall portion of said cavity.

The planar wall portion shall include a reflective surface that includes or is structured as a Littrow arrangement, where the light bundle is intended to fall on said planar wall portion at an angle that lies close to the Blaze angle of the grating.

This creates conditions that allow one or more absorption wavelengths in the light bundle corresponding to the chosen gas to be reflected and diffracted by said planar wall portion in a "straight" opposite direction, wherewith the diffracted absorption wavelengths are again reflected in said curved wall portion as one or more reflected wavelengths and are directed towards said light receiver.

By way of proposed embodiments that lie within the scope of the inventive concept, it is proposed that the curved wall portion shall conform to the curved shape applicable to a parabolic shape.

This enables a physical light source to appear virtually, via a reflector or reflector construction, and to be placed in or close to the focus or focal point of a parabolic shape.

The curved wall portion may then comprise a part of a parabolic arc positioned on one side of the axis of a parabolic shape.

More particularly, it is proposed that the planar grating-allotted cavity wall portion shall include a grating structure that has a Blaze angle for reflection and/or diffraction in a "straight" opposite direction, where the grating structure and other measures may be conveniently adapted for a diffraction grating of a first and possibly a second order.

It is also proposed that the Blaze angle is between 50 and 60°.

It is also proposed, in accordance with the invention, that one or more light receivers can be placed close to the light source and/or close to a virtual light source and that the receiving lobes of the light receiver used are directed towards the curved surface.

More particularly, it is proposed that the cavity is comprised of two polymer-based replicas that have been treated to provide selected wall portions with light reflective properties.

It is also proposed, in accordance with the invention, that the light source shall comprise an incoherent light source for generating a wavelength spectra in the IR range.

It is also proposed, in accordance with the invention, that a physical light source or a virtual light source can be placed close to or in a focal point allocated to the concave curved surface and that one or more light receivers can be placed in or close to said focal point.

It is also proposed, in accordance with the invention, that a physical light source can be placed in one focal point or focus of an elliptic shape or an ellipsoidal shape and that an optical filter is placed in the second focal point or focus and the virtual light source appearing at said second focal point or focus.

The optical filter shall be designed to permit the passage of light-related wavelengths within a free spectral range applicable to the detector system, and more particularly that said optical filter shall be adapted to filter out and to block wavelengths that are shorter than wavelengths co-ordinated in the free spectral range.

Advantages

Those advantages primarily characteristic of the present invention and the particular significant characteristic features thereof reside in the creation of conditions which enable a gas-adapted gas cell to be produced in a simple fashion, in which a cavity, a light source and one or more light receivers are co-ordinated to form a compact unit and are directly adapted to one another for evaluating one or more chosen gases and/or gas mixtures.

A parabolically curved light-reflecting wall portion of the cavity functions to reflect an incoming divergent light bundle as a wave front onto a planar grating-allocated wall portion which, in turn, reflects a diffracted wave front having selected wavelengths back onto the curved surface, which, in turn, reflects diffracted wavelengths onto one or more light receivers so as to enable the concentration of one or more gases and/or gas concentrations to be established with the aid of an evaluated light intensity within a chosen absorption wavelength or chosen absorption wavelengths.

The primary characteristic features of the present invention are defined in the characterising clause of the accompanying claim 1.

BRIEF DESCRIPTION OF THE DRAWING

An embodiment that includes significant characteristic features of the present invention and that is at present preferred will now be described by way of example with reference to the accompanying drawings, in which;

FIG. 6 is a graph showing the variation in efficiency with respect to wavelengths for a Littrow arrangement, and;

FIG. 7 is a graph showing the wavelength-related reception of the detectors in relation to light source emission percentages.

DESCRIPTION OF EMBODIMENTS AT PRESENT PREFERRED

It is pointed out initially that we have chosen to use in the following description of an embodiment at present preferred and including significant characteristic features of the invention and illustrated in the figures of the accompanying drawings, special terms and terminology with the intention of illustrating the concept of the invention more clearly.

However, it will be noted that the expressions chosen here shall not be seen as limited solely to the chosen terms used in the description, and that each term chosen shall be interpreted as also including all technical equivalents that function in at least essentially the same way so as to achieve the same, or essentially the same intention and/or technical effect.

Figure 1:
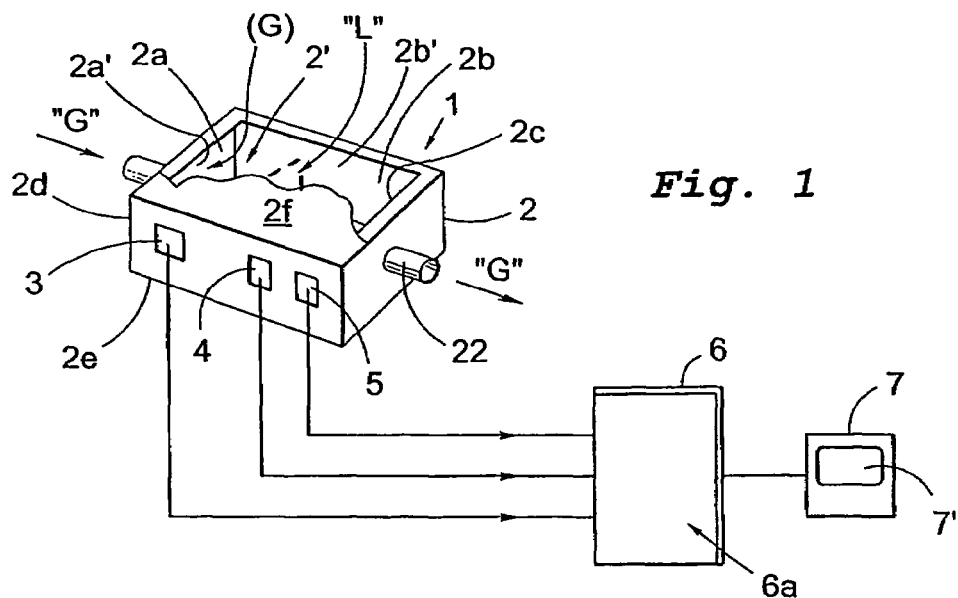
FIG. 1 illustrates in principle and in the form of a block diagram a gas sensor which includes a gas cell that is structured in accordance with the invention's directives and through which a gas can flow, wherein the gas cell includes a light source and two light receivers connected to electronic circuits that include a display unit.

Thus, FIG. 1 illustrates schematically and principally the fundamental conditions for the present invention, where the significant features of the invention have been concretised in an embodiment at present preferred and described in more detail hereinafter.

The principle construction of the gas sensor 1, shown in FIG. 1, is known to the art.

The invention includes primarily the gas cell 2 used with a unique orientation of a physical light source 3 and a unique co-ordination of a number of light receivers, where two side-related light receivers 4 and 5 are shown in the illustrated embodiment.

A person familiar with this technical field will realise that the number of light receivers 4, 5 may vary, as can also their physical placements, depending on the gas or gases chosen or on the gas mixture chosen and also on the shape of the cavity in the gas cell 2.

Consequently, the proposed embodiment is illustrated and described with respect to two side-related light receivers, solely for the sake of simplicity, where one light receiver 4 is placed and adapted in respect of an absorption wavelength corresponding to the chosen gas, while the other light receiver 5 is placed and adapted to serve as a reference wavelength.

As a result, the signal in the receiver 4 can be normalised so as to be generally independent of any variation in the light intensity of the light source 3, such variation occurring at least as the light source 3 ages.

The gas cell 2 of FIG. 1 includes to this end mutually opposed cavity-defining wall portions that have light-reflecting properties. The schematically illustrated wall portions defining the cavity 2' comprise a first side-related wall portion 2a, a second side-related wall portion 2b, a third side-related wall portion 2c and a fourth side-related wall portion 2d.

The side-related wall portions 2a, 2b, 2c and 2d are in co-action with a flat bottom portion 2e and a flat roof portion 2f, that are here seen disposed parallel with one another.

Thus, all surfaces, such as the ones given the reference numerals 2a, 2b, that have been treated to provide light-reflecting properties have been referenced 2a', 2b' and so on and can be referred to as mirror surfaces 2a', 2b' and so on in the following description.

In principle, it is required that a light beam "L", emitted from the light source 3, shall pass the cavity 2' and there be readily reflected by the wall surface or mirror surface 2b' and directed onto and received by the light receiver 4 (or 5) in a known manner. The light beam "L" therewith defines a cavity-enclosed optical measuring path through an enclosed gas sample (G).

Different gases and different gas mixtures require optical measuring paths of mutually different lengths or extremities. This requirement can be met by enlarging the dimensions of the cavity 2' or by creating conditions for a plurality of reflection paths between the light source 3 and the receivers 4 and 5.

Thus, FIG. 1 illustrates, in the form of a block schematic a gas cell 2 through which a gas "G" can flow and which will enclose a gas sample (G) intended for electronic evaluation.

Figure 2:
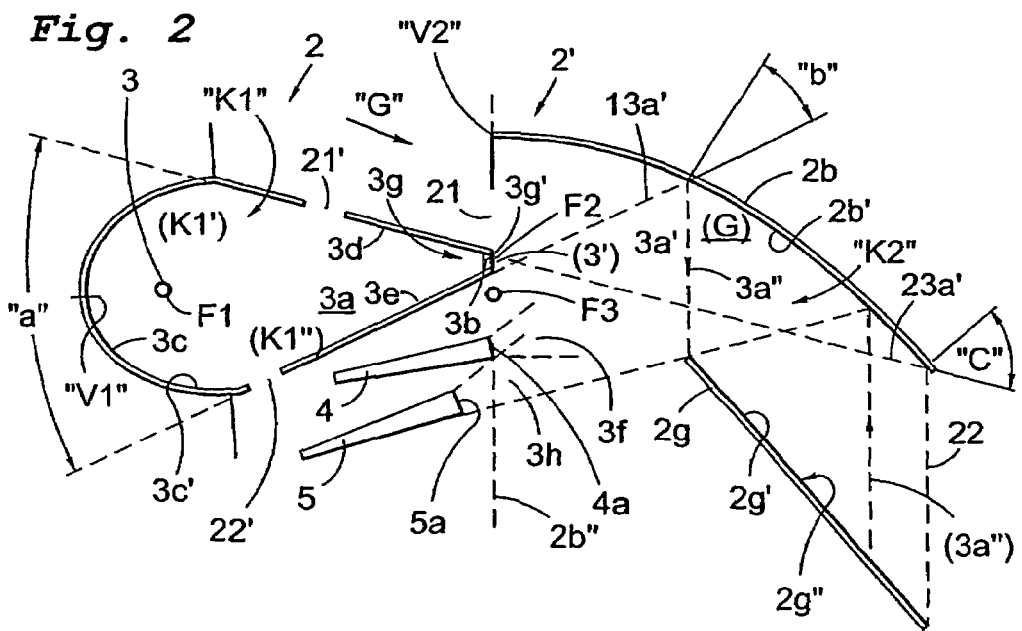
FIG. 2 is a plan view of an enlarged image of the gas cell, showing the cavity construction, the light source and two light receivers, although without including electronic circuits for driving the light source and receiving and evaluating the light intensity for a relevant absorption wavelength or relevant absorption wavelengths related to a chosen gas.

The inventive gas cell 2, shown in FIGS. 1 and 2, is adapted to co-act with electronic circuits 6, coordinated as a unit, so as to enable a gas cell-associated light source 3 to be operated with the aid of said electronic circuits 6 and to detect signals occurring on one or more light receivers 4, 5 and therewith be able to evaluate the instant light intensity related to a chosen absorption wavelength or wavelengths, or, alternatively, related to a chosen reference wavelength or reference wavelengths, and therewith evaluate the presence of a chosen gas "G" and/or the concentration of such a gas.

A display unit 7 is connected to the electronic circuits 6 for showing visually on a display surface or display screen 7' solely the presence of a gas or its concentration.

FIG. 2 is a plan view that shows a gas cell 2 according to the present invention in more detail, the geometry and construction of the gas cell being described in more detail hereinafter.

The gas cell 2, shown in FIG. 2, has a quite complicated configuration and defines primarily the cavity 2' or space that encloses a gas sample (G) to be measured, said cavity 2' being described in more detail hereinafter.

In a first embodiment, the actual optical measuring path is developed within the space designated a second space "K2".

All of the inner wall portions of the cavity 2' (although with the exception of the wall portions 3d, 3e), with associated bottom portion and roof portion, are surface-treated in a known manner to provide highly light-reflective properties.

The gas cell 2 and its cavity 2' shall be considered as a thin structure, in that the wall portions 2a, 2b, 2c and 2d are extremely narrow and in that the bottom portion 2e and the roof portion 2f are placed close together.

In the FIG. 2 embodiment, the height dimension is chosen to correspond to the requisite height of the light source 3, which can be from 3 to 5 mm.

The cavity 2' can be considered to consist of two mutually separate spaces, a first space "K1" that includes a physical light source 3 and a reflector or reflector construction, and a second space "K2" having the primary function of defining a gas sample (G) measuring chamber.

In this case, the cavity 2' and its second space "K2" include a first opening 21 for the entrance of gas G to be measured, and a second opening 22 for the exit or output of the measured gas sample (G).

The first space "K1" is constructed to enclose an omniradiating physical light source 3 which is adapted to emit a convergent light bundle 3a directed onto and through an opening 3b through the medium of a reflector or reflector construction 3c.

The first space "K1" and the reflector 3c have a partially elliptical or ellipsoidal subpart (K1') and a connecting subpart (K1"), which has a tapering shape.

The omniradiating physical light source 3 is placed in one focus or focal point F1 of the elliptical cavity (K1'), wherewith the radiating light rays from the light source 3 will be reflected by the reflector 3c onto a second focus or focal point F2 and there form a virtual image (3') of the physical light source.

In the illustrated case, the second or connecting subpart (K1") is delimited by two convergent wall parts 3d and 3e.

The light rays from the light source 3 are reflected partly towards the focus F2 in an elliptically curved mirror surface belonging to the reflector 3c, and are partly emitted directly onto the focus F2 from the light source 3.

The wall portions 3d and 3e are given a mutually converging form such as to define an opening angle "a" for the first space "K1", and shall be formed or treated to avoid light reflections or, alternatively, to be given deficient reflective properties.

In this latter case, the wall portions 3d, 3e may be "serrated" or "blackened".

A light bundle 3a' having a divergent angle "a" can now be considered to depart from a punctiform virtual light source (3') from said focal point or focus F2 and therewith form within the second space "K2" diverging light beams which are reflected obliquely in a concave wall portion 2b that includes a treated wall surface or mirror surface 2b'. The diverging light bundle 3a' is reflected totally in the concave mirror surface 2b' and therewith adapted to be directed as a "wave front" onto an opposite second flat wall portion 2g, which includes a wall mirror surface 2g' that has been treated for diffraction of received light rays and wavelengths, said wall mirror surface 2g' having a construction that is described in more detail hereinafter.

Figure 5:
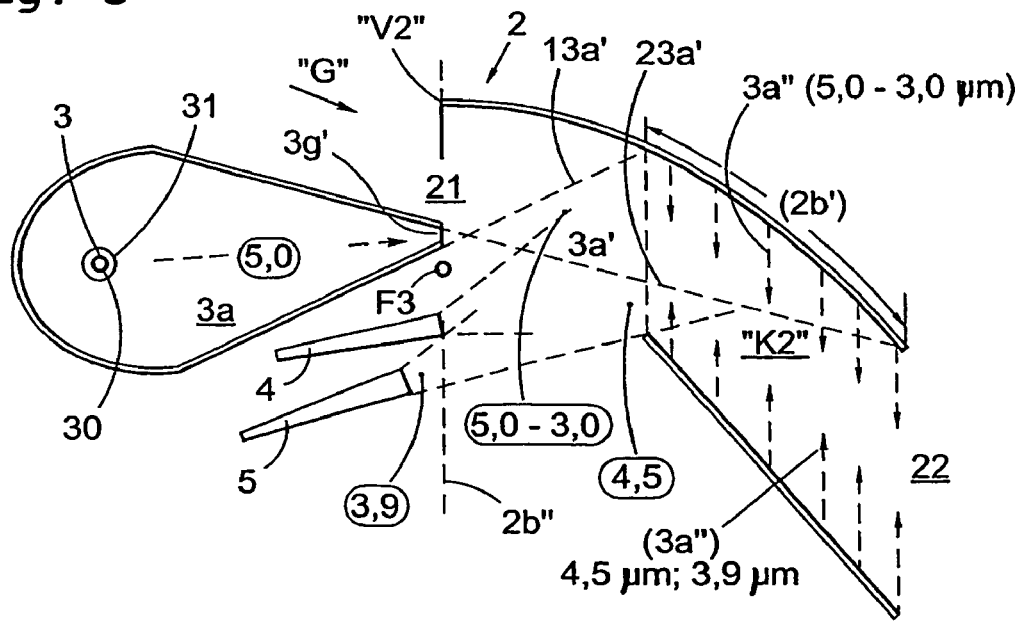
FIG. 5 is a plan view of the gas cell shown in FIG. 2, in which fight reflection and wavelength or light diffraction is shown for a gas cell adapted to determine the presence of carbon dioxide gas and its present concentration.

Diffracted light that has a wave front which includes a chosen wavelength or wavelengths is reflected from the flat wall mirror surface 2g' onto the concave wall surface or mirror surface 2b', from which it is directed back in a direction towards the virtual light source (3'), although with the relevant absorption wavelength or relevant absorption wavelengths directed to impinge on one or more light receivers, such as the light receivers 4 and 5, in a manner which is described in more detail hereinafter, with reference to FIGS. 5, 6 and 7.

The light receiver 4 and each other light receiver that is used (such as the light receiver 5 and other light receivers not shown) are designed to receive and detect the light intensity in the diffracted absorption wavelength corresponding to the gas sample (G), whereas remaining light receivers detect the instant light intensity in respect of their allocated absorption wavelengths in a similar manner.

The flat grating-allocated cavity-associated wall mirror surface 2g' thus presents a light-reflecting and light-diffracting or wavelength-diffracting surface, where said surface is treated and given the reference numeral 2g" and structured as a Littrow arrangement.

The total light wave 3a" containing parallel light rays and reflected by the wall mirror surface 2b' is caused to fall onto said wall portion 2g and said wall mirror surface 2g' and 2g" at an angle of incidence that lies close to the Blaze angle of the grating.

The conditions for causing a "Littrow" arrangement and to arrange for a "Blaze" angle are defined in the publication Springer Series in Chemical Physics, Volume 5, Laser Spectroscopy, on pages 132 and 134.

With regard to the space "K2" and the gas sample (G) enclosed therein, the optical length of the light bundle 3a', the optical length of the reflective wave front 3a", the diffracted wave front (3a"'), the reflected and diffracted light rays from the concave mirror surface 2b' among other things to the receiver 4 will constitute the total, effective optical measuring path or extremity through the enclosed gas sample (G).

According to one proposed second embodiment of the inventive gas cell 2, the length of the measuring path can be increased by also including an optical measuring path in the first space "K1", by causing the gas G to also pass through an opening 21' and out through an opening 22'.

Each chosen wavelength in the light bundle 3a' and in the wave front 3a" can now be reflected and diffracted by said flat wall mirror surface 2g' and 2g" in a "straight" opposite direction as a diffracted light wave front having discrete wavelengths, referenced (3a"'), and thereafter reflected by the curved mirror surface 2b' with the wavelengths mutually separated, and therewith allowed to pass to said light receiver 4 as an absorption-wavelength-related light bundle 3f.

By "straight" opposite direction is meant an insignificant directional difference and a reflection angle that deviates only slightly from "zero".

In this respect, it is important that the chosen absorption wavelength to be measured will not appear in or close to the virtual light source (3').

The shape of the curved wall mirror surface 2b' in FIG. 2 conforms to the curved shape applicable to a mathematical parabolic function.

Light rays to and from the reflector or reflector surface 3c converge onto the focusing or focal point F2 through the medium of a convergent light bundle 3a, therewith exposing the virtual light source (3'), which may be orientated in or preferably in the close proximity of a focusing point or focal point F3 of the parabolically shaped curved wall mirror surface 2b'.

The curved wall mirror surface 2b' is thus comprised of a wall portion (2b') (See FIG. 5) having the shape of a parabolic arc and positioned on one side of an axis 2b" of the parabolic shape.

The grating structured surface 2g" on the wall surface 2b' is, similar to other measures, adapted as a diffraction grating of the first order.

The Blaze angle is dependent on the chosen absorption wavelength and will, in practice, have a value of between 50 and 60°.

In the case of the FIG. 2 embodiment, two slightly separated light receivers 4, 5 are placed externally of the first space "K1" and in the close proximity of the virtual light source (3'), and the reception lobes 3f and 3h of respective receivers are directed towards the curved mirror surface 2b' and the indicated wall portion (2b') so as to be able to receive different absorption wavelengths representative of the gas or gases.

More particularly, it is proposed, in accordance with the invention, that the cavity 2' may be formed of two polymer-based replicas that have been treated in a separate process to impart good light reflective properties to the wall portions and wall mirror surfaces.

The light source 3 is also comprised of an incoherent light source for generating a wavelength spectrum in the IR range, wherewith the light source 3 may have the form of an incandescent filament 30, surrounded by silica glass 31.

The reflector 3c in FIG. 2 is formed along an elliptical line 3c' as a flat elliptically curved surface that extends slightly beyond one focus point F1 by a distance corresponding to a chosen value between said focus point F1 and a vertex "V1".

The curved elliptical line 3c' terminates at a point distal from the two converging flat wall portions 3d and 3e, which connect the curved line 3c' with the second focusing point F2 such as to leave a small opening 3g, (3b), for instance an opening measuring about 1.2-0.3 min, such as 0.6 mm, at said second focusing point F2.

The wall portions 3d and 3e have a serrated or sawtooth surface, so as to be able to absorb or reflect away undesirable disturbances light that fall outside the desired opening angle "a" for the light bundle 3a' generated and directed by the light source 3 and/or via reflections of incident light back to the elliptically curved mirror line 3c' or the surface 3c.

The elliptically curved flat surface 3c and the converging wall portions 3d and 3e of the aforedescribed arrangement are mutually so dimensioned that a divergent light bundle 3a' exiting through the opening 3g, with an optical filter 3g' mounted therein, will obtain a divergent angle "a" of between 30 and 45°, such as about 40°.

The light bundle 3a', leaving the opening 3g, is divergent with edge-allocated light rays referenced 13a', 23a'.

The curved surface 2b and the mirror surface 2b' are adapted as a parabolic line with the origo in a vertex point "V2" and with an axis 2b" orientated through, or at least close to, the opening 3g and the focusing point or focal point F2.

The curved surface 2b and the mirror surface 2b' form a chosen part or portion (2b') of one half of a parabolic line with its focal point or focus referenced F3.

The focus F2 and the focus F3 may conveniently coincide in one embodiment of the invention, although they have been shown in the illustrated embodiment to be displaced slightly from one another along the axis 2b", as will be described in more detail hereinafter.

The wave front 3a" reflected in the mirror surface 2b' is reflected towards the grating surface 2g" and is diffracted so as to return to the mirror surface 2b' as a diffracted wave front (3a") and therewith be reflected onto a respective light receiver 4 and 5 as two diffracted light bundles 3f and 3h with their respective absorption wavelengths, among other things.

The reflection angle "b" for the first edge-related light ray 13a' of the light bundle 3a' will preferably be between 20° and 40°, preferably between 25° and 35°, such as about 30°.

The reflection angle "C" for the second edge-related light ray 23a' of the light bundle 3a' will preferably be between 40° and 80°, preferably between 50° and 70°, such as about 60°.

More particularly, the focal point or focus F2 and the opening 3g are placed closer to the focus F3, although in a direction towards the vertex "V2", whereas the opening 4a serving the receiver 4 that receives the light bundle within the receiving lobe 3f is placed on the other side of the focus F3.

The receiver 5, with its opening 5a, is adapted to receive selected light rays of chosen frequency within the receiving lobe 3h, these selected light rays serving as a reference signal in the electronic circuit 6.

It will be apparent from the aforedescribed FIG. 2 embodiment that a plurality of other light receivers, similar to the receiver 4 and/or the receiver 5, may be separated physically and distributed in a manner which permits the detection of different absorption wavelengths or absorption frequencies corresponding to and significant in respect of other chosen gases.

Although the light receivers 4 and 5 are shown to be placed beneath the first space "K1", it will be understood that said receivers may alternatively be placed above the space "K1".

Figure 3:
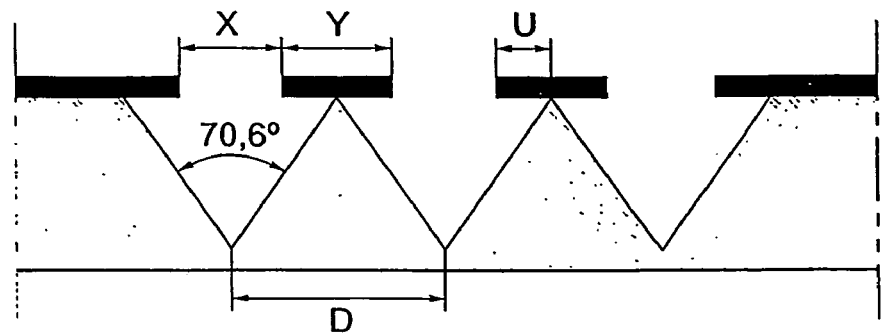
FIG. 3 illustrates a chosen system design and Blaze angle, where said design and angle are chosen with a view to a grating structure present in crystalline silica.
Figure 4:
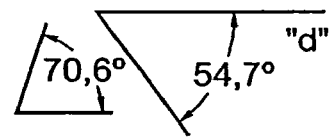
FIG. 4 illustrates more precisely a used embodiment of a Littrow arrangement allocated to a planar light-reflecting and wavelength-diffracting wall portion.

As will be evident from FIGS. 3 and 4, the choice of system design and Blaze angles for the planar grating-allocated cavity-associated wall surface 2g" have been made, inter alia, with the view of the grating structure in crystalline silica forming two different crystal planes with a mutual angle of 70.6°, which can be used to create a diffraction grating with a natural Blaze angle "d" of 54.7°.

This enables an original required for tool manufacture to be created in an inexpensive and readily producible manner, and also to provide a polymer-based replica.

The reference sign X in FIG. 3 identifies a resist/oxide opening, while the reference sign Y identifies a resist/oxide bridge.

The value referenced U is equal to Y/2 during the etching process, while reference D represents a value for the grating constant.

FIG. 4 illustrates a Littrow arrangement in more detail, said figure comprising an enlargement of a delimited subsection of the planar surface 2g' that includes the grating structure 2g".

In the Littrow arrangement, an incoming light wave 3a" is allowed to fall in at an angle, which is close to the Blaze angle of the grating.

The light rays in the light wave 3a" that have a predetermined absorption wavelength determined by the gas sample (G) chosen and of significance to the invention are reflected diffracted in essentially the "straight" opposite direction at a very small reflection angle, therewith creating conditions for achieving maximum efficiency, as illustrated in FIG. 6.

In the case of a diffraction grating of the first order, the wavelength is equal to the function "2D sin 55°", which results in an efficiency close to 100% in the case of this embodiment, since no higher order is found.

Neither are there any negative orders in the case of such high angles of incidence.

Thus, there are created conditions, which enable all light having a predetermined absorption wavelength to be reflected back (3a") in a desired direction, and further to a respective light receiver 4 and 5.

With regard to focus F2 for the elliptical shape and the absorption-wavelength-related reception within the receivers 4 and 5, the receivers may not be permitted to coincide but that a small distance therebetween is necessary, it being possible to control this small distance in the illustrated embodiment by placing focus F2 on one side of focus F3 and the receivers 4 and 5 on the other side of focus F3.

Should focus F2 coincide with focus F3, it is necessary to angle the planar grating surface 2g" or the grating constant D to some extent, so that the diffracted light bundle (3a") will be reflected obliquely in the mirror surface 2b' and with respective absorption wavelengths directed towards the receiver 4 or the receiver 5.

Should the receiver 4 or the receiver 5 be placed in the focus F3, it is also necessary to place the focus F2 on one side of the focus F3.

Thus, the invention enables a light source 3 or a visual light source (3') to be placed conveniently in or close to a focal point or focus F3 assigned to the concave curved surface 2b'.

Alternatively, one or more light receivers 4, 5 may be placed adjacent to or in a focal point F3 allocated to the concave curved mirror surface 2b'.

The optical filter 3g' is adapted to permit the passage of light-related wavelengths within a free spectral area applicable to the detector system, wherein the filter 2g' is adapted to filter out wavelengths that are shorter than wavelengths co-ordinated in the free spectral range.

By free spectral range is meant a spectral range, which is illuminated solely by one spectral order in a calculation point and is therewith free from shorter and overlapping wavelengths of another order or orders.

More specifically, the optical filter 2g' shall shadow wavelengths that are shorter than a chosen shortest wavelength.

In the event that higher orders of fundamental frequencies are received by the receivers 4, 5, these frequencies will be understood as noise. Measures should therefore be taken to prevent the occurrence of frequencies of each higher order.

The invention will now be explained more specifically with reference to an application according to FIG. 5, where a specially designed and adapted gas cell 2 and gas sensor shall detect the carbon dioxide content of air with a normal gas mixture. Other adaptations and another design of the gas cell 2 and its cavity 2' are required for the detection and assaying of other gases.

The gas "G" passes through the inlet 21 and through the space "K2" in the cavity 2' and through the outlet 22.

A white light source is chosen for the light source 3, which includes, inter alia, the wavelength ranges that are characteristic of the absorption wavelengths of $CO_2$.

Although an incandescent lamp or some other thermal light source 3 has been proposed, the concept of the invention also enables the use of light-emitting diodes.

Carbon dioxide has a characteristic absorption wavelength of 4.25 µm. This wavelength shall be diffracted out and received in the receiver 4, whereas a shorter wavelength, say 3.9 µm, shall be received in the receiver 5 and there serve as a reference signal.

A second order wavelength will then be 2.12 µm and the filter 3g' is intended to filter out these wavelengths and shorter wavelengths.

The electronic circuit 6 evaluates the light intensity in the receivers 4 and 5 and the presence of the $CO_2$ gas is established through the medium of comparison circuit 6a together with the concentration of the gas, which is displayed on the display surface 7'.

FIG. 5 shows the light spectrum and the optical measurement path applicable to the evaluation of $CO_2$ gas in a gas mixture present in the cavity or the space "K2".

FIG. 5 also shows the current values of the wavelengths in question.

The incandescent wire 30 is surrounded by quartz glass 31, there being defined an upper limit of 5.0 µm The lower limit of, say, 3.0 µm is defined by the optical filter 3g'.

The wave front 3a" is reflected and directed onto the planar surface 2g' containing the Littrow arrangement surface 2g" wherefrom the wavelength 4.0-4.5µ and 3.9µ are diffracted (3a") and received by respective receivers 4 and 5 subsequent to reflection by the mirror surface 2b'.

FIG. 6 is a graph showing the change in efficiency with respect to the wavelength for a Littrow arrangement, from which it will be seen that the efficiency is high in respect of the wavelength concerned.

FIG. 7 is a graph illustrating the wavelength-related reception of the detectors for receivers 4 and 5 in relation to the percentage of light source emission, said graph showing the high reception for the wavelengths around 4.0µ and 4.5µ.

It will also be seen from FIG. 5 that the active subpart (2b') of the curved surface 2b or said parabolic shape between the light rays 13a' and 23a' shall be located at a distance from the vertex "V2" of a parabolic line and in the close proximity of the focus or the focal point F3 of said line.

The subpart (2b') is delimited to a point or to a section orientated at right angles or close to a right angle in relation to an axis 2b" of a parabolic line or parabolic function and through a focus or focal point F3 related to said axis.

It will be understood that the invention is not restricted to the aforedescribed exemplifying embodiment and that modifications can be made within the scope of the inventive concept illustrated in the accompanying Claims.

The invention claimed is:

1. In a gas cell included in a gas sensor and adapted to establish the presence of one or more gases and to determine the concentration of such a gas, wherein the gas cell includes a cavity which is defined by wall portions that have light reflecting properties and which is intended to enclose a volume of said gas, wherein there is included a light source which is adapted to emit a light bundle directed for reflection between cavity-associated wall portions and opposing wall portions, and wherein the light bundle is comprised of light rays that are reflected in a concave wall portion and directed towards one or more light receivers which are adapted to detect the occurring light intensity in one or more absorbent wavelengths corresponding to the gas, the improvement which comprises in that the concave curved wall portion is adapted to reflect an obliquely received diverging light bundle from the light source on a flat grating-allocated cavity-associated wall portion whose reflective surface presents a Littrow arrangement or a structured Littrow arrangement; in that the light bundle is adapted to fall on said flat wall portion at an angle which lies close to the Blaze angle of the grating; and in that one or more absorption wavelengths in the light bundle corresponding to the gas chosen are caused to be reflected and diffracted by said flat wall portion in a straight opposite direction such that diffracted wavelengths are reflected in said curved surface and directed towards said light receivers.

2. A gas cell according to claim 1, wherein said curved wall portion conforms to a part of a curved shape representing a parabola.

3. A gas cell according to claim 2, wherein the light source appears virtually in or adjacent to a focal point of a parabolic shape.

4. A gas cell according to claim 2, wherein said curved wall portion has the shape of a parabolic arc orientated on one side of the axis of a parabolic shape.

5. A gas cell according to claim 1, wherein the flat grating allocated cavity-associated wall portion includes a grating structure that has a Blaze angle for reflection of light in an opposite direction.

6. A gas cell according to claim 5, wherein the grating structure is adapted to create a diffraction grating solely of a first order and/or of a second order.

7. A gas cell according to claim 1, wherein the Blaze angle is between 50° and 60°.

8. A gas cell according to claim 1, wherein one or more light receivers are placed close to a virtual light source with their receiving lobes directed towards the curved surface.

9. A gas cell according to claim 1, wherein the cavity is formed by at least one polymer based replica that has been treated to give the wall portions light-reflective properties.

10. A gas cell according to claim 1, wherein the light source is comprised of an incoherent light source for generating a wavelength spectrum within the IR range.

11. A gas cell according to claim 1, wherein a light source or virtual light source is placed in or close to a focal point allocated to the concave curved surface.

12. A gas cell according to claim 1, 8 or 11, wherein said one or more light receivers (4, 5 are placed in the close proximity of or in a focal point allocated to the concave curved surface).

13. A gas cell according to claim 1 including a physical light source is placed in one focal point of an elliptical shape and in that a virtual light source appears in the second focal point and is positioned in an opening that includes an optical filter.

14. A gas cell according to claim 13, wherein the optical filter is adapted to allow the passage of light-related wavelengths within a free spectral range applicable to the detector system.

15. A gas cell according to claim 13, wherein the optical filter is adapted to filter out wavelengths that are shorter than wavelengths co-ordinated in the free spectral range.

16. A gas cell according to claim 1, wherein said cavity has the form of two spaces, where one space includes a physical light source and a reflector.

17. A gas cell according to claim 16, wherein said second space serves the function of a measuring chamber that provides light reflections.

18. A gas cell according to claim 17 wherein said measuring path of the measuring chamber is extended by using an optical measuring path inside the first space.

19. A gas cell according to claim 18, wherein said first space includes an inlet and an outlet for the gas (G) to be measured.

20. A gas cell according to claim 16, wherein said first space has a subpart that is partially elliptical in shape.

21. A gas cell according to claim 20, wherein a terminating subpart has a tapering shape.

22. A gas cell according to claim 21, wherein said subpart is delimited by two convergent wall portions.

23. A gas cell according to claim 22, wherein said wall portions are prepared or formed to exhibit deficient reflective properties.

24. A gas cell according to claim 22, wherein said converging wall portions define an angle corresponding to a divergent angle or opening angle for a light bundle emitted from the light source.

25. A gas cell according to claim 1, wherein a plurality of light receivers are co-ordinated on one side of a cavity-associated space.

26. A gas cell according to claim 25, wherein a number of light receivers are co-ordinated on mutually opposite side of said space.

27. A gas cell according to claim 1, wherein said flat grating-allocated cavity-associated wall portion is given a direction in which a virtual extension connects with or passes closely adjacent to the vertex of the concave curved wall portion.

* * * * *